United States Patent
Ootani et al.

(10) Patent No.: US 7,477,379 B2
(45) Date of Patent: Jan. 13, 2009

(54) ANALYSIS APPARATUS

(75) Inventors: Ryoichi Ootani, Yokohama (JP); Makoto Ishibashi, Nasushiobara (JP)

(73) Assignees: Kabushiki Kaisha Toshiba, Tokyo (JP); Toshiba Electron Tubes & Devices Co., Ltd., Tochigi-ken (JP)

( * ) Notice: Subject to any disclaimer, the term of this patent is extended or adjusted under 35 U.S.C. 154(b) by 0 days.

(21) Appl. No.: 11/819,254

(22) Filed: Jun. 26, 2007

(65) Prior Publication Data

US 2007/0252985 A1 Nov. 1, 2007

Related U.S. Application Data

(63) Continuation of application No. PCT/JP2006/321809, filed on Oct. 25, 2006.

(30) Foreign Application Priority Data

Oct. 26, 2005 (JP) .............................. 2005-311436

(51) Int. Cl.
*G01J 3/30* (2006.01)
(52) U.S. Cl. ...................................... 356/318
(58) Field of Classification Search .................. 356/318
See application file for complete search history.

(56) References Cited

U.S. PATENT DOCUMENTS 5,112,127 A * 5/1992 Carrabba et al. ............. 356/301

2006/0017920 A1 * 1/2006 Tsuchiya et al. ............ 356/317

FOREIGN PATENT DOCUMENTS

| JP | 58-219437 | 12/1983 |
|----|-----------|---------|
| JP | 62-47959 U | 3/1987 |
| JP | 2000-310596 | 11/2000 |
| JP | 2002-529713 | 9/2002 |
| JP | 2005-140529 | 6/2005 |

OTHER PUBLICATIONS

International Search Report dated Jan. 23, 2007 for Appln. No. PCT/JP2006/321809 filed Oct. 25, 2006.

* cited by examiner

*Primary Examiner*—Kara E Geisel
(74) *Attorney, Agent, or Firm*—Pillsbury Winthrop Shaw Pittman, LLP

(57) ABSTRACT

Pulse laser light transmitted through a laser light transmission optical fiber to an optical system unit passes through a distribution reflecting mirror and is condensed by a condenser lens group. The condenser lens group irradiates the condensed laser light onto an analysis object. The fluorescence emitted as a result of the irradiation of the pulse laser light onto the analysis object is condensed by the condenser lens group and is reflected by the distribution reflecting mirror. The optical system unit transmits the fluorescence reflected by the distribution reflecting mirror through an fluorescence transmission optical fiber to a fluorescence measuring instrument. The fluorescence measuring instrument determines the quantity of elements included in the analysis object on the basis of the fluorescence.

8 Claims, 10 Drawing Sheets

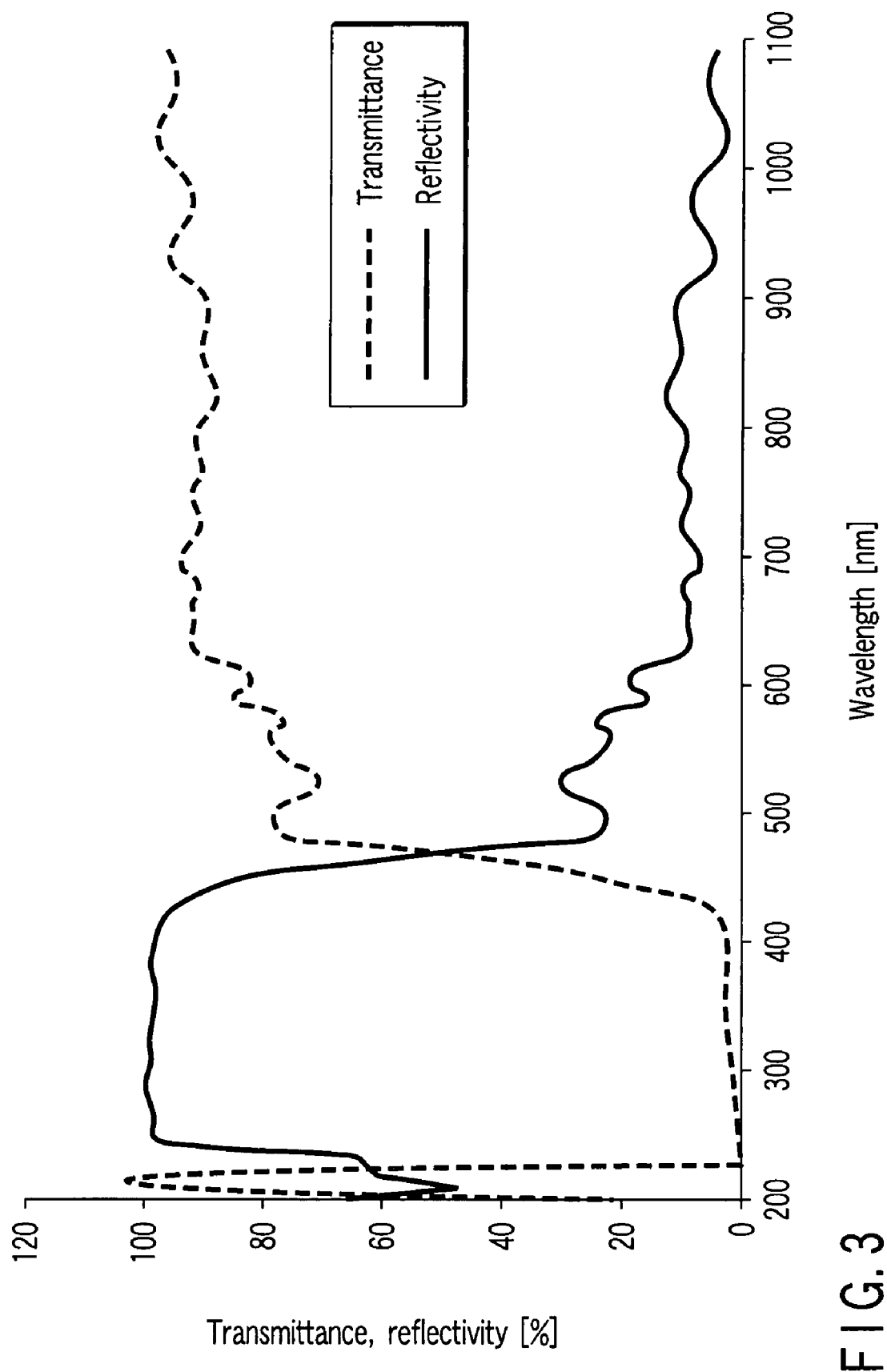
F I G. 3

ANALYSIS APPARATUS

CROSS-REFERENCE TO RELATED APPLICATIONS

This is a Continuation Application of PCT Application No. PCT/JP2006/321809, filed Oct. 25, 2006, which was published under PCT Article 21(2) in English.

This application is based upon and claims the benefit of priority from prior Japanese Patent Application No. 2005-311436, filed Oct. 26, 2005, the entire contents of which are incorporated herein by reference.

BACKGROUND OF THE INVENTION

1. Field of the Invention

This invention relates to an analysis apparatus which analyzes elements on the basis of fluorescence obtained from plasma produced by the irradiation of laser light.

2. Description of the Related Art

One known analysis apparatus irradiates laser light onto an analysis object and determines the quantity of fluorescence produced by the irradiation of laser light, thereby making it possible to analyze the elements of the analysis object with no pretreatment in as short an analysis time as about 100 milliseconds, which enables real-time analysis (e.g., refer to (FIGS. 4 and 5 in page 6 of) Jpn. Pat. Appln. KOKAI Publication No. 2000-310596).

The analysis apparatus condenses laser light with a laser light condensing optical system and irradiates the condensed laser light onto the surface of an analysis object, thereby turning the elements at the surface of the analysis object into plasma. As soon as the irradiation of laser light has ended, the plasma starts to recombine, with the result that the constituent elements of the analysis object turn into excited-state atoms in several microseconds to several tens of microseconds. When the exited-state atoms transit to a lower level, fluorescence whose amount is proportional to the number of atoms is emitted at a wavelength peculiar to the atoms. Then, part of the fluorescence emitted from the analysis object is condensed by the fluorescence condensing optical system from the lateral direction of the laser light condensing optical system. The fluorescence is analyzed spectroscopically by a fluorescence measuring instrument, thereby analyzing the elements included in the substance that emitted the fluorescence.

Furthermore, the use of optical fiber for both of the transmission of laser light and the transmission of fluorescence improves the flexibility of analysis, which provides an analysis apparatus having superior characteristics to those of, for example, a fluorescence X-ray analysis apparatus. When laser light is transmitted through an optical fiber, the irradiation area (or analysis area) of laser light is limited, since transmittable laser light energy is limited because the optical fiber can be damaged if laser light energy to be transmitted is excessive, and since examination results have shown that an energy density of about 25 mJ/mm$^2$ or more is required to produce plasma by the irradiation of laser light. However, the limitation of the laser light irradiation area provides the advantage of assuring the flexibility of analysis.

As described above, in the analysis apparatus, the use of optical fiber for both of the transmission of laser light and the transmission of fluorescence assures the flexibility of analysis. However, when fluorescence is condensed by the fluorescence condensing optical system from the lateral direction of the laser light condensing optical system and is transferred through an optical fiber, the surface of the analysis object must be so flat that the collection of fluorescence is not impeded. If the surface of the analysis object is irregular or has a curvature, the fluorescence condensing optical system that condenses fluorescence from the lateral direction of the laser light condensing optical system cannot condense fluorescence sufficiently, which might make analysis difficult.

It is, accordingly, an object of the present invention to provide an analysis apparatus which permits only a small decrease in the sensitivity due to the effect of the shape of an analysis object, enables the analysis accuracy to be improved, makes it possible to integrate the laser light condensing optical system and the fluorescence condensing optical system with each other to make the system more compact, and further enables the collection of fluorescence to be adjusted easily.

BRIEF SUMMARY OF THE INVENTION

According to one aspect of the present invention, there is provided an analysis apparatus characterized by comprising: a laser light transmission optical fiber which transmits laser light; an optical system unit which includes distribution means for allowing the laser light transmitted through the laser light transmission optical fiber to pass through and reflecting fluorescence emitted as a result of the irradiation of the laser light onto an analysis object and condensing irradiation means for not only condensing the laser light passed through the distribution means and irradiating the condensed laser light onto the analysis object but also condensing the fluorescence from the analysis object and guiding the condensed fluorescence to the distribution means; a fluorescence transmission optical fiber which transmits the fluorescence reflected by the distribution means; and analysis means for determining quantity of elements included in the analysis object on the basis of the fluorescence transmitted through the fluorescence transmission optical fiber.

According to another aspect of the present invention, there is provided an analysis apparatus characterized by comprising: a laser light transmission optical fiber which transmits laser light; an optical system unit which includes distribution means for allowing the laser light transmitted through the laser light transmission optical fiber to pass through and reflecting fluorescence emitted as a result of the irradiation of the laser light onto an analysis object, condensing irradiation means for not only condensing the laser light passed through the distribution means and irradiating the condensed laser light onto the analysis object but also condensing the fluorescence from the analysis object and guiding the condensed fluorescence to the distribution means, and reflecting means for reflecting the fluorescence reflected at the distribution means in a direction different from the direction in which the fluorescence was reflected; a fluorescence transmission optical fiber which transmits the fluorescence reflected by the reflecting means; and analysis means for determining quantity of elements included in the analysis object on the basis of the fluorescence transmitted through the fluorescence transmission optical fiber.

According to still another aspect of the present invention, there is provided an analysis apparatus characterized by comprising: a laser light transmission optical fiber which has a laser light output face for outputting laser light and transmits laser light and outputs laser light at the laser light output face; a fluorescence transmission optical fiber which has a fluorescence entrance face that fluorescence enters and allows fluorescence to enter the fluorescence entrance face and transmits the fluorescence; an optical system unit which has condensing irradiation means for not only condensing the laser light output from the laser light output face of the laser light transmission optical fiber and irradiating the condensed laser light onto the analysis object but also condensing fluorescence emitted from the analysis object as a result of the irradiation of the laser light and guiding the condensed fluorescence to the fluorescence entrance face of the fluorescence transmission optical fiber; and analysis means for determining the quantity of elements included in the analysis object on the basis of the fluorescence transmitted through the fluorescence transmission optical fiber.

BRIEF DESCRIPTION OF THE SEVERAL VIEWS OF THE DRAWING

FIG. 3 is a graph showing the relationship between the wavelength, transmittance, and reflectivity of a distribution mirror in the analysis apparatus according to the first embodiment of the present invention;

DETAILED DESCRIPTION OF THE INVENTION

Figure 1:
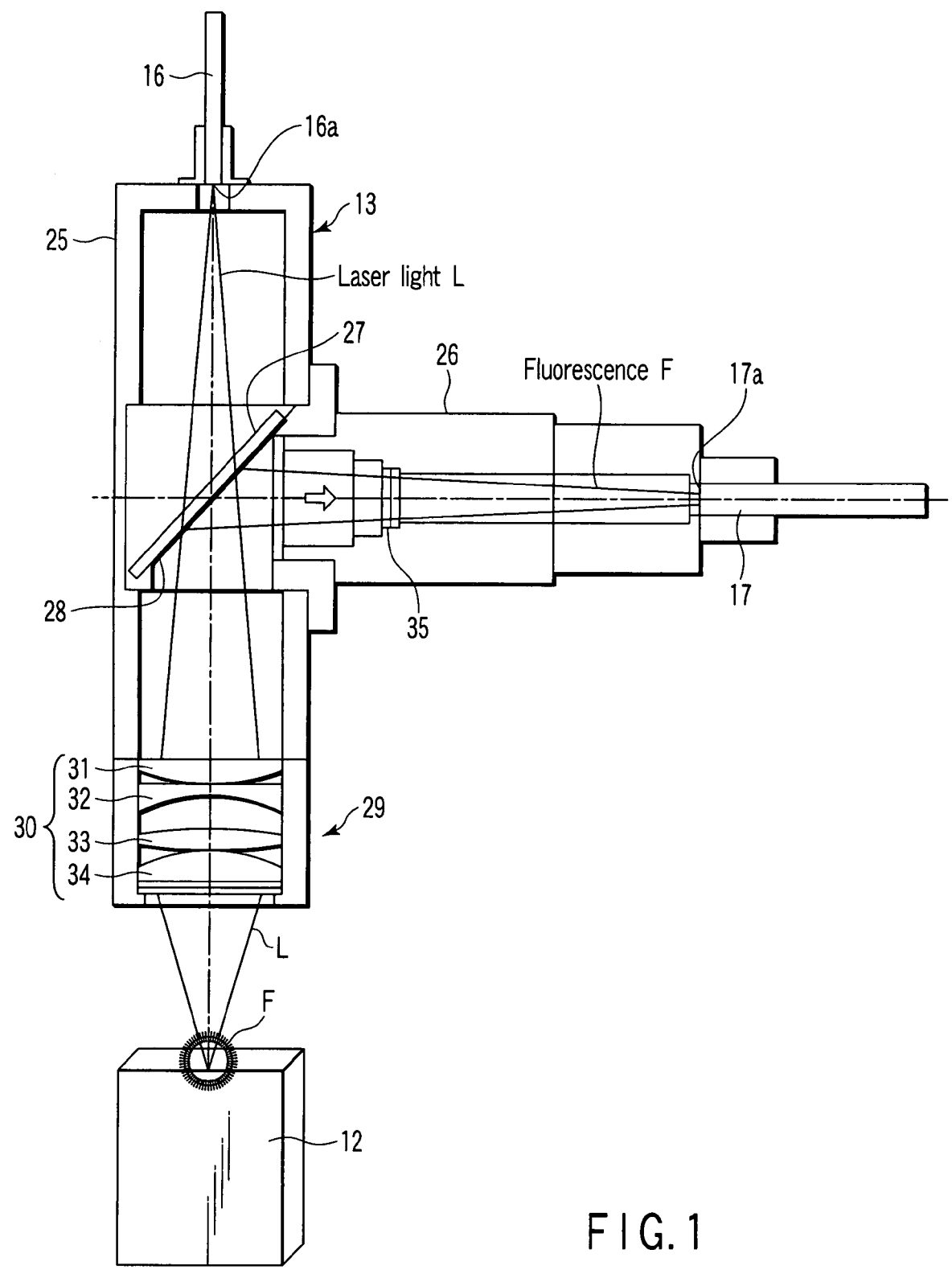
FIG. 1 is a sectional view of an optical system unit of an analysis apparatus according to a first embodiment of the present invention.
Figure 2:
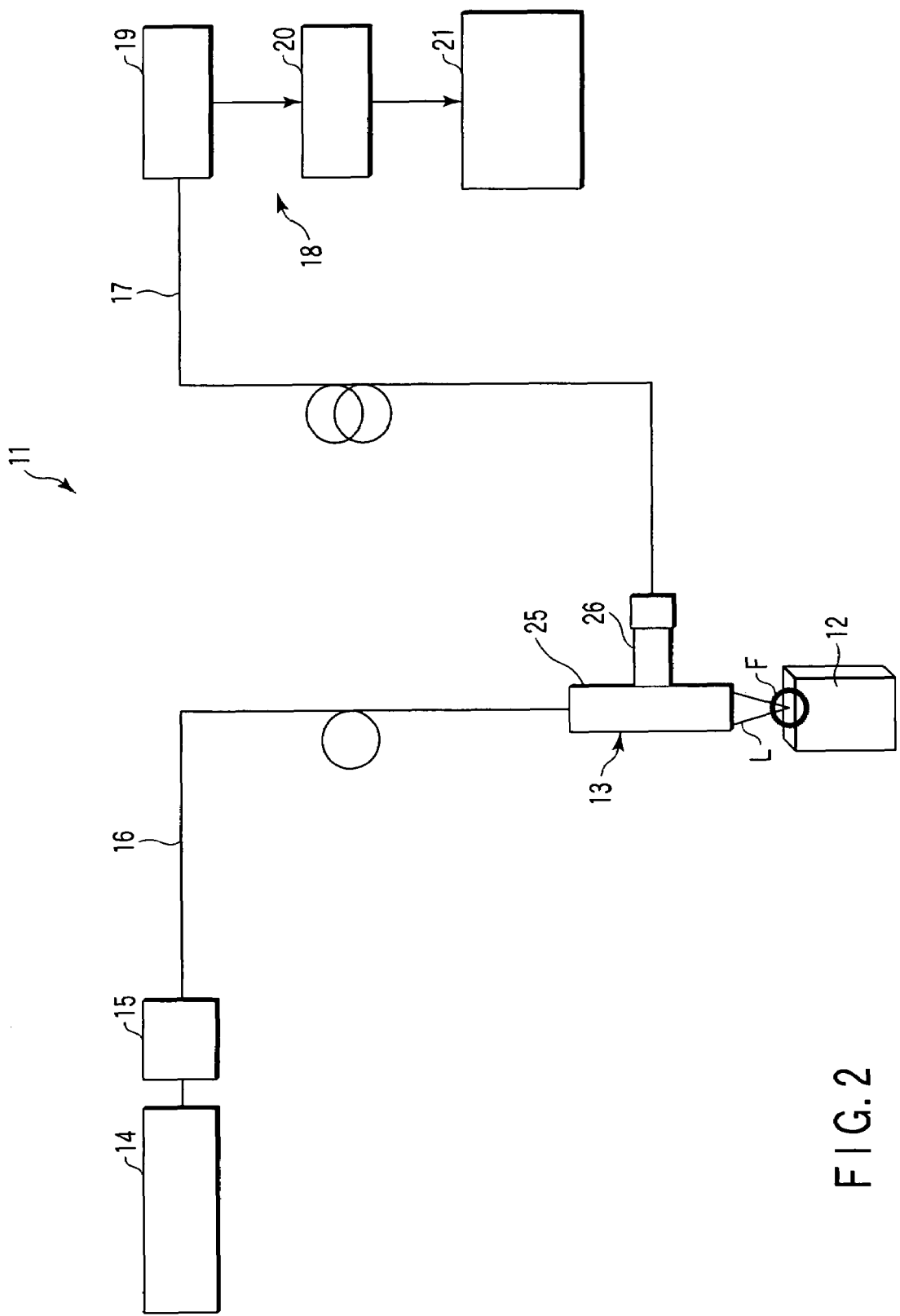
FIG. 2 shows the configuration of the analysis apparatus according to the first embodiment of the present invention.

Hereinafter, referring to the accompanying drawings, embodiments of the present invention will be explained. FIGS. 1 to 3 show a first embodiment of the present invention. As shown in FIG. 2, an analysis apparatus 11 causes an optical system unit 13 to irradiate pulse laser light L as laser light onto an analysis object 12, collect fluorescence F produced as a result of the surface of the analysis object 12 turning into plasma, and determine the quantity of the elements contained in the analysis object from the wavelength and intensity of the fluorescence F.

The analysis apparatus 11 includes a YAG laser oscillator 14 as a laser oscillator which oscillates pulse laser light L, such as YAG (Yttrium•Aluminium•Garnet) laser light. The YAG laser oscillator 14 outputs pulse laser light L with a specific pulse width on the basis of a driving pulse generated with specific timing by a main control unit as control means (not shown).

In the YAG laser oscillator 14, there is provided an optical fiber incidence system 15 as an optical system which collects oscillated pulse laser light L. The pulse laser light L collected by the optical fiber incidence system 15 is caused to enter one end of a laser light transmission optical fiber 16.

Connected to the optical system unit 13 are not only the other end of the laser light transmission optical fiber 16 to transmit pulse laser light L to the optical system unit 13 but also one end of a fluorescence transmission optical fiber 17 which the fluorescence F collected by the optical system unit 13 enters and through which transmits the fluorescence is transmitted.

Connected to the other end of the fluorescence transmission optical fiber 17 is analysis means 18 which determines the quantity of the elements contained in the analysis object 12 on the basis of fluorescence F transmitted through the fluorescence transmission optical fiber 17. Connected to the analysis means 18 are a fluorescence measuring instrument 19 which disperses the fluorescence F transmitted through the fluorescence transmission optical fiber 17 and measures all of the wavelengths and intensities and a computer 20 which determines the elements contained in the analysis object 12 and their quantities from the measured values obtained at the fluorescence measuring instrument 19. A display unit 21 which displays the result of analysis or the like is connected to the computer 20. The operation timing of each of the fluorescence measuring instrument 19 and computer 20 is controlled by a timing adjusting mechanism (not shown).

Furthermore, as shown in FIG. 1, the optical system unit 13 includes a cylindrical body tube 25 with the optical axis of pulse laser light L as an axis line. On the side of the body tube 25, a fluorescence light guiding tube 26 with its axis line in a direction crossing the optical axis of pulse laser light L, specifically in the direction perpendicular to the optical axis, is provided so as to provide a continuous hole.

To the rear anchor, one end, of the body tube 25, the other end of the laser light transmission optical fiber 16 is connected. From the laser light output face 16a, the other end, of the laser light transmission optical fiber 16, pulse laser light L is output to the inside of the body tube 25. The optical axis of the pulse laser light L is made identical with the axis line of the body tube 25.

Inside the body tube 25, in a position facing the fluorescence light guiding tube 26 in the optical path of the pulse laser light L, a distribution reflecting mirror 27 is provided as distribution means which causes the pulse laser light L to pass through to the other end, or the tip, of the body tube 25 and reflects the fluorescence F collected from the tip of the body tube 25 toward the fluorescence light guiding tube 26. The distribution reflecting mirror 27, which is formed into a flat plate, is provided in such a manner that it inclines at an angle of, for example, 45° to the optical axis of the pulse laser light L. A surface which is opposite to the surface facing the laser light output face 16a of the laser light transmitting optical fiber 16 in the distribution reflecting mirror 27 and faces the tip of the body tube 25 is configured to be a fluorescence reflecting surface 28 which reflects fluorescence L including visible light and ultraviolet light. FIG. 3 shows the relationship between the wavelength, transmittance, and reflectivity of the distribution reflecting mirror 27 which distributes pulse laser light L and fluorescence F.

In the body tube 25, there is provided condensing irradiation means 29 which not only condenses the pulse laser light L transmitted via the laser light transmission optical fiber 16 and irradiates the pulse laser light onto the analysis object 12 but also condenses the fluorescence F emitted from the atoms contained in the surface of the analysis object and guides the fluorescence to the fluorescence transmission optical fiber 17. The condensing irradiation means 29, which is provided at the tip of the body tube 25 on the optical axis of the pulse laser light L passed through the distribution reflecting mirror 27, includes a condenser lens group 30, a condensing irradiation optical system, as condensing means which condenses the pulse laser light L and irradiates the light L onto the analysis object 12. The condenser lens group 30 includes a first lens 31 which is a convex lens whose laser light entrance face is flat and whose laser light output face projects convexly, a second lens 32 which is a concave lens whose laser light entrance face is projects convexly and whose laser light output face dents concavely, a third lens 33 which is a convex lens each of whose laser light entrance face and laser light output face projects convexly, and a fourth lens 34 which is a convex lens whose laser light entrance face project convexly and whose laser light output face is flat.

The fluorescence F emitted as a result of the irradiation of pulse laser light L onto the analysis object 12 is caused to enter the condenser lens group 30. The fluorescence F is condensed and guided to the fluorescence reflecting surface 28 of the distribution reflecting mirror, which reflects the fluorescence toward the fluorescence light guiding tube 26. Accordingly, the condenser lens group 30 is also a fluorescence condensing optical system as fluorescence condensing means for condensing the fluorescence F emitted from the atoms contained in the surface of the analysis object 12 on which pulse laser light L was irradiated.

At the tip of the fluorescence light guiding tube 26, one end of the fluorescence transmission optical fiber 17 is connected and held in such a manner that the fluorescence entrance face 17a at one end of the fluorescence transmission optical fiber 17 is provided so as to correspond to the position of the optical axis of the fluorescence F, the axis line of the fluorescence light guiding tube 26. In the fluorescence light guiding tube 26, there is provided a fluorescence condenser lens 35 as light guiding means for collecting the fluorescence F reflected by the fluorescence reflecting surface 28 of the distribution reflecting mirror 27 and guided into the fluorescence light guiding tube 26 and guiding the collected light to the fluorescence entrance face 17a of the fluorescence transmission optical fiber 17.

Next, an examination method of analyzing the elements of the analysis object 12 with the analysis apparatus 11 of the first embodiment will be explained. After the analysis object 1 is set in a specific position, the YAG laser oscillator 14 outputs pulse laser light L. The output pulse laser light L is collected by the optical fiber incidence system 15 and then is transmitted through the laser light transmission optical fiber 16 to the optical system unit 13.

The pulse laser light L transmitted to the optical system unit 13 passes through the distribution reflecting mirror 27 and is condensed by the condenser lens group 30, which irradiates the condensed pulse laser light onto the surface of the analysis object 12.

The surface of the analysis object 12 is heated to a high temperature instantaneously as a result of the irradiation of the pulse laser light L and is turned into plasma. Accordingly, plasma is produced at the surface of the analysis object 12.

Thereafter, the irradiation of the pulse laser light L from the YAG laser oscillator 14 is stopped.

As soon as the irradiation of the pulse laser light L has been stopped, the plasma produced at the surface of the analysis object 12 starts to recombine and the elements in the analysis object 12 become atoms, while remaining in the excited state in several microseconds to several tens of microseconds. Then, when the atoms in the excided state transit to lower levels, the atoms emit fluorescence F proportional to the number of atoms.

The emitted fluorescence F enters the condenser lens group 30. The condenser lens group 30 condenses the fluorescence F. Then, the fluorescence F is reflected by the fluorescence reflecting surface 28 of the distribution reflecting mirror 27 and is guided into the fluorescence light guiding tube 26. The fluorescence F guided into the fluorescence light guiding tube 26 is condensed by the fluorescence condenser lens 35 and then is guided to the fluorescence entrance face 17a of the fluorescence transmission optical fiber 17.

The fluorescence F guided through the fluorescence transmission optical fiber 17 is transmitted to the fluorescence measuring instrument 19. The fluorescence measuring instrument 19 disperses the fluorescence F and measures all of the wavelengths and intensities. From the measured values obtained at the fluorescence measuring instrument 19, the computer 20 finds out the elements included in the analysis object 12 and their quantities and displays the result of the analysis or the like on the display unit 21.

As described above, since the condenser lens group 30 of the condensing irradiation means 29 can not only condense the pulse laser light L to be transmitted through the laser light transmission optical fiber 16 and irradiate the condensed laser light onto the analysis object 12 but also condense the fluorescence F emitted from the atoms contained in the surface of the analysis object 12 as a result of the irradiation of the pulse laser light L and transmit the condensed fluorescence F to the fluorescence transmission optical fiber 17, the sensitivity decreases less due to the effect of the shape of the analysis object 12, which enables the precision of analysis to be improved.

Using the condenser lens group 30 in both of the collection of the pulse laser light L and that of the fluorescence F enables the condenser lens group 30 to be integrated into the optical system unit 13, which make the optical system unit more compact. Moreover, adjusting the focus position of the pulse laser light L enables the focus adjustment of the fluorescence F to be made automatically, which makes it possible to make adjustments easily at the time of analysis.

Figure 4:
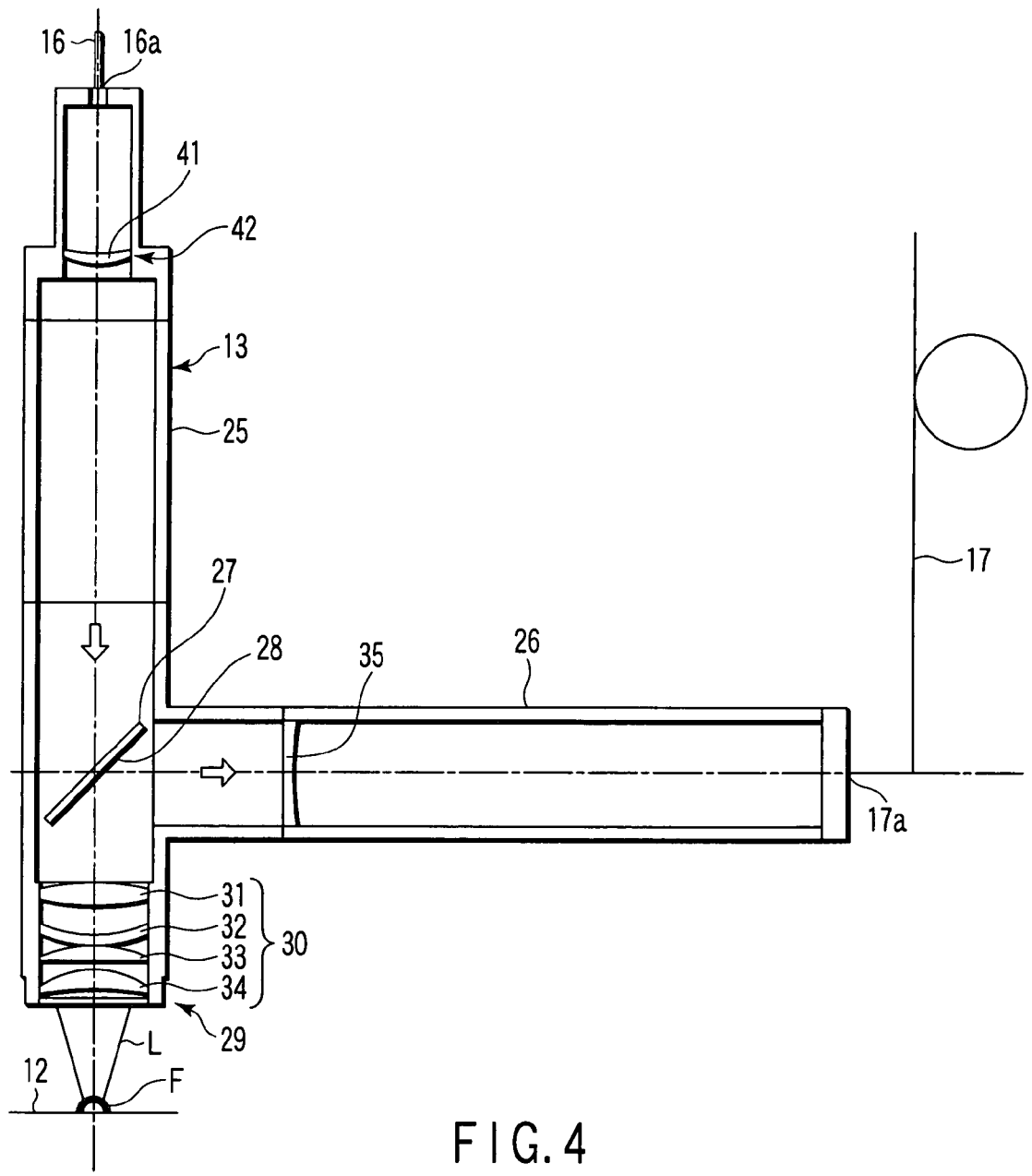
FIG. 4 is a sectional view of an optical system unit of an analysis apparatus according to a second embodiment of the present invention.
Figure 5:
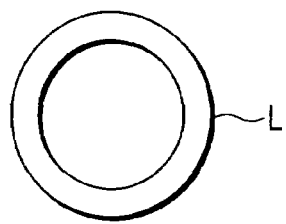
FIG. 5 is an explanatory diagram of laser light irradiated by the analysis apparatus of the second embodiment.

Next, FIGS. 4 and 5 show a second embodiment of the present invention. Condensing irradiation means 29 includes a conical lens 42 as shaping means 41 for shaping pulse laser light L into an annulus and a condenser lens group 30 as condensing means for condensing the pulse laser light L shaped into an annulus by the conical lens 42.

The conical lens 42 is provided on the rear anchor side of the body tube 25 of an optical system unit 13. The condenser lens group 30 is provided at the tip of the body tube 25 of the optical system unit 13. A distribution reflecting mirror 27 is provided between the conical lens 42 and the condenser lens group 30 in such a manner that it is closer to the tip of the body tube 25 of the optical system unit 13.

The condenser lens group 30 includes a first lens 31 which is a convex lens whose laser light entrance face and laser light output face project convexly, a second lens 32 which is a concave lens whose laser light entrance face dents concavely and whose laser light output face projects convexly, a third lens 33 which is a convex lens whose laser light entrance face projects convexly and whose laser light output face is flat, and a fourth lens 34 which is an concave lens whose laser light entrance face projects convexly and whose laser light output face dents concavely.

Then, the pulse laser light L transmitted through the laser light transmission optical fiber is shaped into a uniform annulus by the conical lens 42 and passes through the distribution reflecting mirror 27. Then, the annular pulse laser light is collected by the condenser lens group 30, which irradiates the condensed laser light onto the surface of the analysis object 12. FIG. 5 shows an annular pulse laser light L with an outside diameter of, for example, 1 mm or more and 5 mm or less irradiated onto the surface of the analysis object 12.

For example, suppose the analysis object 12 is a coin-shaped lithium coin battery. When the leakage of the lithium electrolyte from the lithium coin battery is checked for by irradiating pulse laser light L, it is necessary to check for the presence or absence of the leakage of the lithium electrolyte by one irradiation of pulse laser light L to improve the efficiency of the check. Moreover, if pulse laser light L with considerable energy is transmitted through the laser light transmission optical fiber 16, the laser light transmission optical fiber 16 can be damaged. Therefore, pulse laser light L with considerable energy cannot be transmitted through the laser light transmission optical fiber 16. Accordingly, the pulse laser light irradiation area is limited, because the laser energy of the pulse laser light L transmitted is limited by the laser light transmission optical fiber 16. The result of tests has shown that the production of plasma by the irradiation of pulse laser light L requires an energy density of about 25 mJ/mm$^2$. Therefore, it is difficult to do checking by irradiating circular pulse laser light L onto the lithium coin battery once. To overcome this difficulty, it has been found that collecting pulse laser light L in an annulus makes it possible to satisfy an energy density of about 25 mJ/mm$^2$ or more at which plasma is produced by the irradiation of pulse laser light L and do checking by one irradiation of annular pulse laser light L.

However, when annularly collected pulse laser light L is irradiated onto the lithium coin battery, annular plasma is produced from the lithium coin battery. Annular fluorescence F is produced from the annular plasma. Therefore, the annular fluorescence F has to be measured with a uniform sensitivity. It is not easy to measure the annular fluorescence F uniformly. Specifically, in a conventional ordinary analysis apparatus where a laser irradiation optical system and a fluorescence condensing optical system are provided separately, when a measurement is made by irradiating pulse laser light L particularly in the range of a diameter of 1 mm or more, the sensitivity changes so greatly that an accurate measurement cannot be made.

To overcome this problem, after the pulse laser light L transmitted through the laser light transmission fiber is shaped into a uniform annulus by the conical lens 42, the shaped laser light is caused to pass through the distribution reflecting mirror 27. Then, the annular laser light is condensed by the condenser lens group 30, which irradiates the condensed laser light onto the surface of the analysis object 12. Moreover, fluorescence F emitted from the lithium coin battery as a result of the irradiation of pulse laser light L onto the lithium coin battery is condensed by the condenser lens group 30. The fluorescence F is reflected by the fluorescence reflecting surface 28 of the distribution reflecting mirror 27 and is guided via the fluorescence condenser lens 35 to the fluorescence transmission optical fiber 17.

As a result, even if the irradiation range of annular pulse laser light L onto the lithium coin battery is made wider, the fluorescence F emitted from a wide range on the lithium coin battery is condensed by the condenser lens group 30 and is reflected by the distribution reflecting mirror 27 and then is guided to the fluorescence transmission optical fiber 17, which makes it possible to efficiently determine the quantity of elements included in all of the laser light irradiation range. At the same time, the fluorescence F emitted from the wide range of the lithium coin battery can be measured with almost the same sensitivity. That is, since the annular fluorescence F emitted as a result of the irradiation of the annular pulse laser light L can be measured with a uniform sensitivity, the leakage of lithium electrolyte in all of the laser irradiation range of the lithium coin battery can be measured. Consequently, the lithium coin battery can be analyzed with high accuracy over a wide range.

Figure 6:
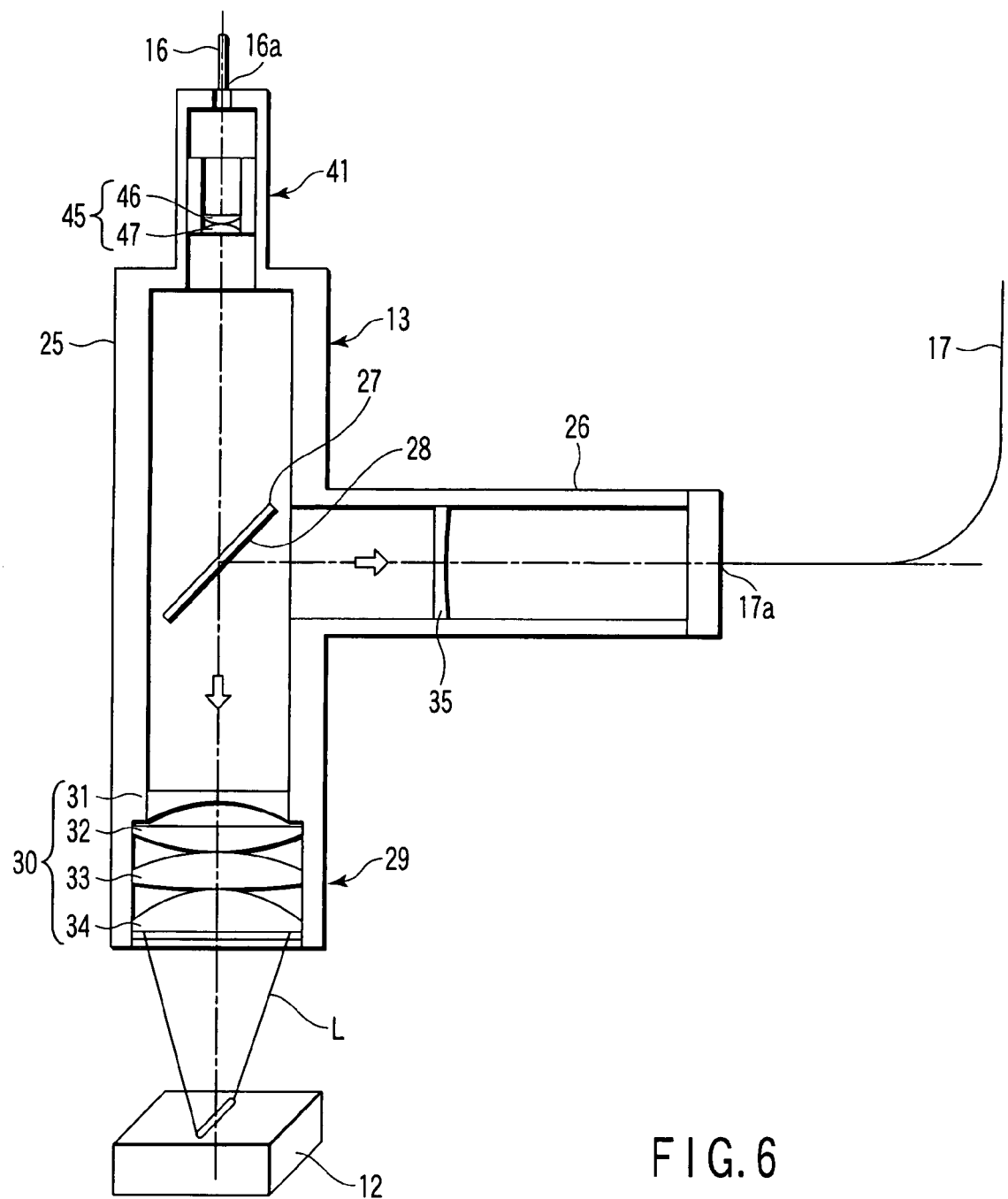
FIG. 6 is a sectional view of an optical system unit of an analysis apparatus according to a third embodiment of the present invention.

FIG. 6 shows a third embodiment of the present invention.

Condensing irradiation means 29 includes a toroidal lens group 45 as shaping means 41 for shaping pulse laser light L into a line and a condenser lens group 30 as condensing means for condensing the pulse laser light L shaped into a line by the toroidal lens group 45.

The toroidal lens group 45 is provided on the rear anchor side of the body tube 25 of an optical system unit 13. The condenser lens group 30 is provided at the tip of the body tube 25 of the optical system unit 13. A distribution reflecting mirror 27 is provided between the toroidal lens group 45 and the condenser lens group 30 in such a manner that it is closer to the tip of the body tube 25 of the optical system unit 13.

The toroidal lens group 45, which has a first toroidal lens 46 and a second toroidal lens 47, shapes pulse laser light L into a line whose longitudinal length is, for example, 1 mm or more and 5 mm or less, specifically a long, thin, flat ellipse.

The condenser lens group 30 includes a first lens 31 which is a concave lens whose laser light entrance face projects so as to be an almost flat, convex surface and whose laser light output face dents so as to be a concave surface, a second lens 32 which is a convex lens whose laser light entrance face projects so as to be an almost flat, convex surface and whose laser light output face projects so as to be a convex surface, a third lens 33 which is a convex lens whose laser light entrance face projects so as to be a convex surface and whose laser light output face projects so as to be an almost flat, convex surface, and a fourth lens 34 which is a third toroidal lens whose laser light entrance face projects so as to be a convex surface and whose laser light output face is flat.

Then, the pulse laser light L transmitted through the laser light transmission optical fiber 16 is shaped into a line by the toroidal lens group 45 and passes through the distribution reflecting mirror 27. Then, the line-shaped pulse laser light is condensed by the condenser lens group 30, which irradiates the condensed laser light onto the surface of the analysis object 12.

As described above, since irradiating the line-shaped pulse laser light L onto the analysis object 12 enables the fluorescence L emitted in a line from the analysis object 12 to be measured with a uniform sensitivity, it is possible to produce the same operational effect as that of the second embodiment.

Figure 8:
FIG. 8 is an explanatory diagram of laser light irradiated by the analysis apparatus of the fourth embodiment.
Figure 7:
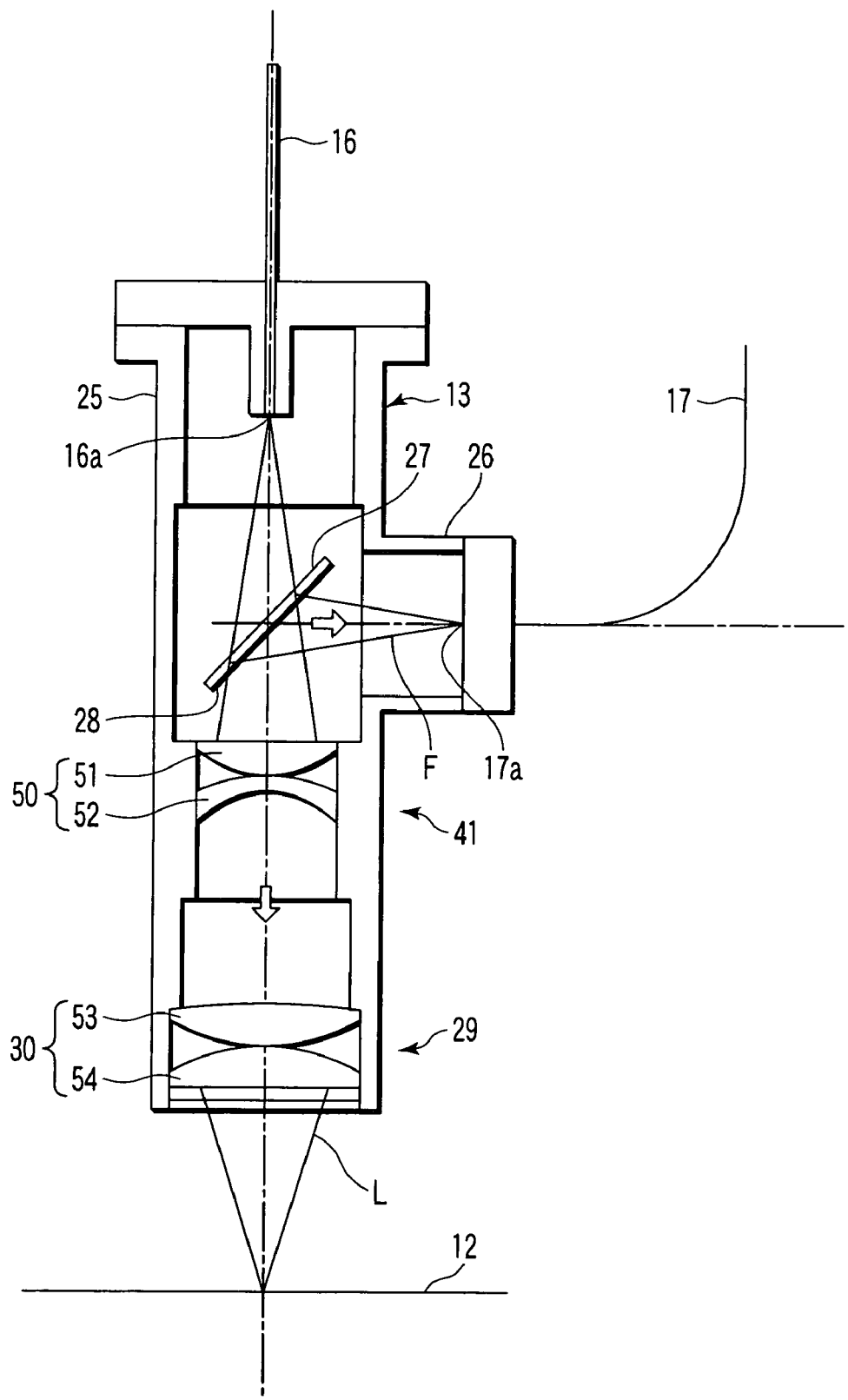
FIG. 7 is a sectional view of an optical system unit of an analysis apparatus according to a fourth embodiment of the present invention.

FIGS. 7 and 8 show a fourth embodiment of the present invention. The condenser lens group 30 of an optical system unit 13 condenses pulse laser light L into circular pulse laser light L with a diameter ($\phi$) of 1 mm or more and 2.5 mm or less and then irradiates the circular pulse laser light onto an analysis object 12.

In a body tube 25 closer to the tip than the distribution reflecting mirror 27 of an optical system unit 13, there is provided a lens group 50 as shaping means 41 for shaping the pulse laser light L passed through the distribution reflecting mirror 27 by polarizing the pulse laser into parallel beams. The lens group 50 has a first lens 51 whose top side is flat and whose bottom side projects so as to be a convex surface and a second lens 52 whose top side projects so as to be a convex surface and whose bottom surface dents so as to be a concave surface.

On the optical path of the circular parallel pulse laser light L passed through the lens group 50, there is provided a condenser lens group 30 which condenses the circular parallel pulse laser light L into a circle, an irradiation aperture with a diameter (φ) of, for example, 1 mm or more and 2.5 mm or less and irradiates the condensed pulse laser light L onto an analysis object 12. The condenser lens group 30 has a third lens 53 which is a convex lens whose top side and bottom side each project so as to be a convex surface and a fourth lens 54 whose top side projects so as to be a convex surface and whose bottom side is flat.

Then, the pulse laser light L transmitted through the laser light transmission optical fiber 16 is shaped into a circle by the first lens group 50 and passes through the distribution reflecting mirror 27. Then, the circular pulse laser light is condensed by the condenser lens group 30, which irradiates the condensed laser light onto the surface of the analysis object 12. FIG. 8 shows circular pulse laser light L with a diameter (φ) of 1 mm or more and 2.5 mm or less irradiated onto the surface of the analysis object 12.

As described above, since irradiating the pulse laser light L condensed into a circular point onto the analysis object 12 enables the fluorescence L emitted in a circle from the analysis object 12 to be measured with a uniform sensitivity, it is possible to produce the same operational effect as that of the second embodiment.

Figure 9:
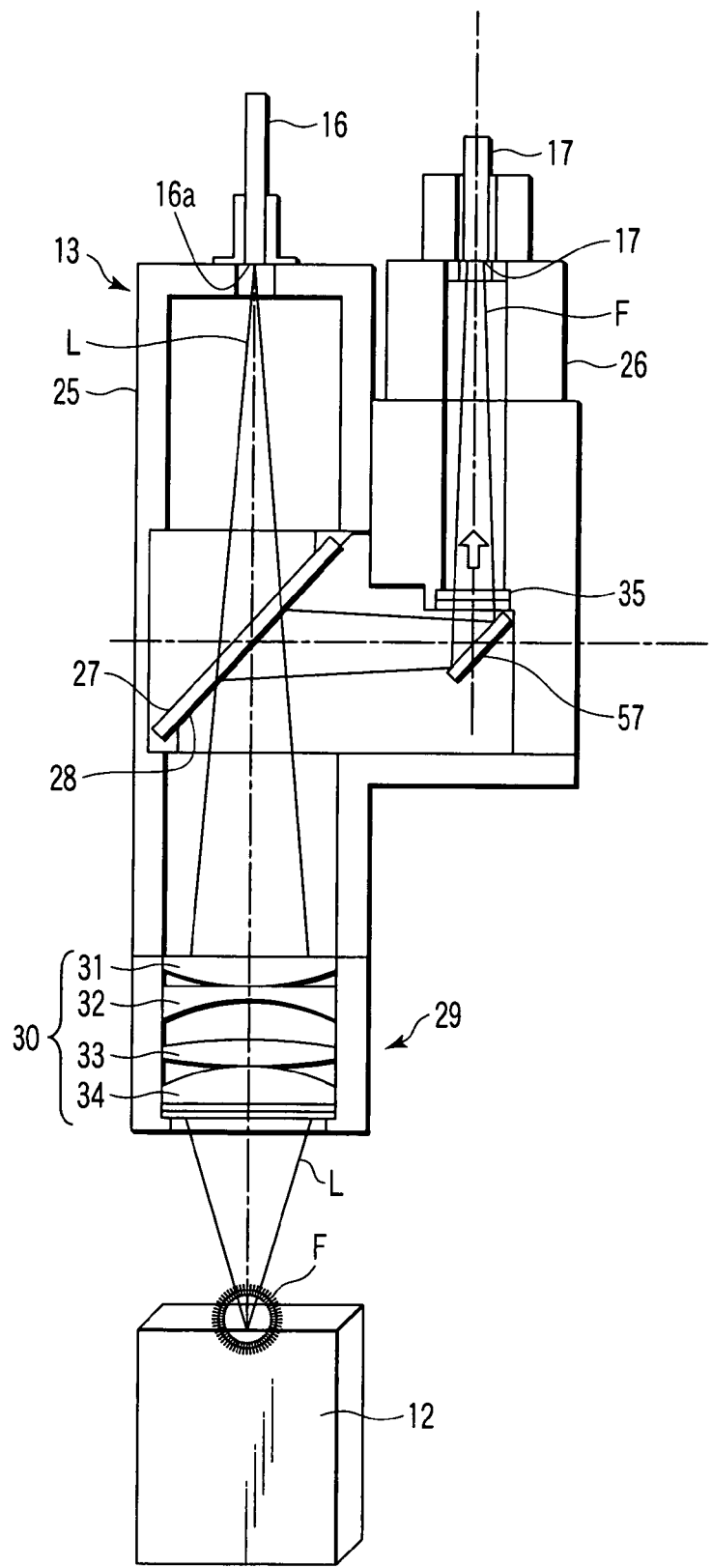
FIG. 9 is a sectional view of an optical system unit of an analysis apparatus according to a fifth embodiment of the present invention.

Next, FIG. 9 shows a fifth embodiment of the present invention. In an optical system unit 13, a fluorescence light guiding tube 26 is provided on the side of a body tube 25 in such a manner that its axis line is in parallel with the axis line of the body tube 25. The rear anchor, or one end, of the fluorescence light guiding tube 26 is provided almost in the same position as that of the rear anchor of the body tube 25. The other end, or the tip, of the fluorescence light guiding tube 26 is communicated with and opens into the intermediate portion of the body tube 25.

One end of the fluorescence transmission optical fiber 17 is connected to and held at the rear anchor of the fluorescence light guiding tube 26. The fluorescence entrance face 17a at one end of the fluorescence transmission optical fiber 17 is provided so as to correspond to a position on the axis line of the fluorescence light guiding tube 26.

At the tip of the fluorescence light guiding tube 26, there are provided a reflecting mirror 57 as reflecting means for reflecting fluorescence F reflected by the fluorescence reflecting surface 28 of the distribution reflecting mirror 27 and guided into the fluorescence light guiding tube 26 toward the fluorescence entrance face 17a of the fluorescence transmission optical fiber 17 in such a manner the fluorescence F travels along the axis line of the fluorescence light guiding tube 26 and a fluorescence condenser lens 35 that condenses the fluorescence F reflected by the reflecting mirror 57 and guides the condensed fluorescence F to the fluorescence entrance face 17a of the fluorescence transmission optical fiber 17.

The configuration excluding the fluorescence light guiding tube 26 and reflecting mirror 57 is the same as that of the first embodiment.

Then, the pulse laser light L transmitted through the laser light transmission optical fiber 16 passes through the distribution reflecting mirror 27 and is condensed by the condenser lens group 30 and is irradiated onto the surface of the analysis object 12.

The fluorescence F emitted from the atoms contained in the surface of the analysis object 12 enters the condenser lens group 30. The condenser lens group 30 condenses the fluorescence F. The condensed fluorescence L is reflected by the fluorescence reflecting surface 28 of the distribution reflecting mirror 27 and is guided to the fluorescence light guiding tube 26. The fluorescence F guided into the fluorescence light guiding tube 26 is reflected by the reflecting mirror 57 and is condensed by the fluorescence condenser lens 35. The condensed fluorescence is guided to the fluorescence entrance face 17a of the fluorescence transmission optical fiber 17.

As described above, the fluorescence F reflected by the fluorescence reflecting surface 28 of the distribution reflecting mirror 27 and guided into the fluorescence light guiding tube 26 is reflected by the reflecting mirror 57, thereby making it possible not only to arrange the body tube 25 of the optical system unit 13 in parallel with the fluorescence light guiding tube 26 but also to make the connection direction of the optical fiber 16 to the optical system unit 13 the same as that of the optical fiber 17, which enables the optical system unit 13 to be made more compact.

Figure 10:
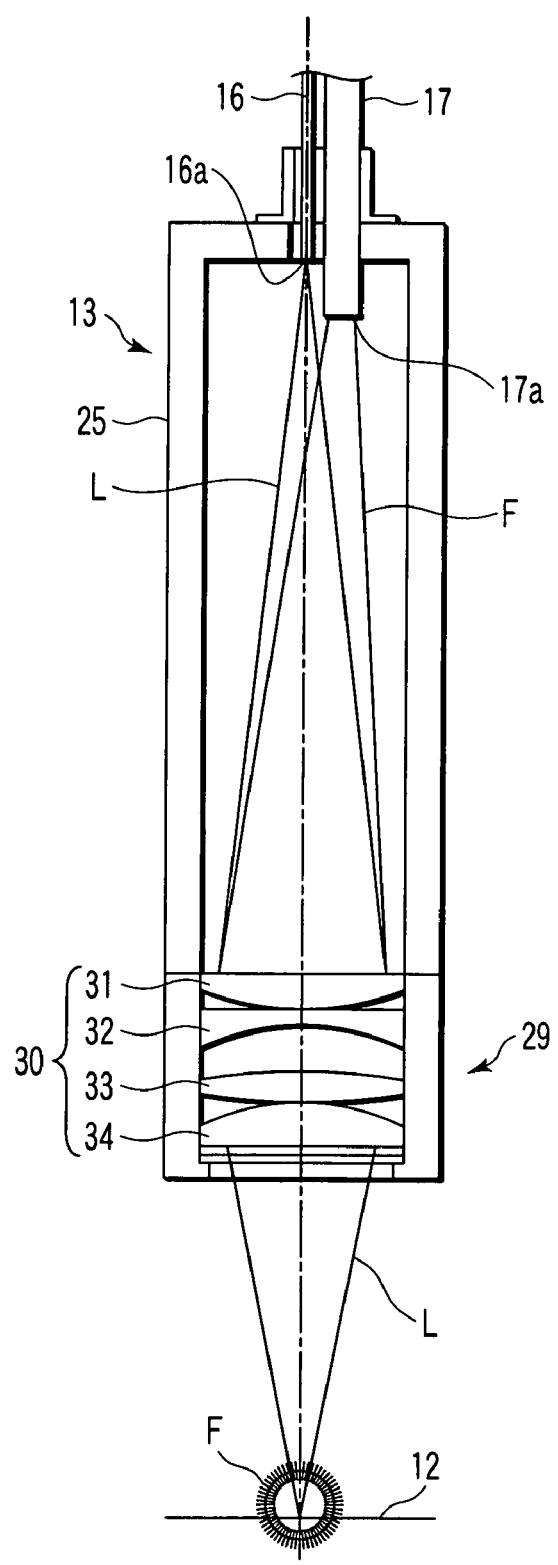
FIG. 10 is a sectional view of an optical system unit of an analysis apparatus according to a sixth embodiment of the present invention.

Next, FIG. 10 shows a sixth embodiment of the present invention. An optical system unit 13 has a body tube 25. At the rear anchor of the body tube 25, there are provided a laser light transmission optical fiber 16 and a fluorescence transmission optical fiber 17. At the tip of the body tube 25, there is provided a condenser lens group 30.

The laser light transmission optical fiber 16 is provided so as to correspond to the position of the axis line of the body tube 25. The fluorescence transmission optical fiber 17 is provided on the side of the laser light transmission optical fiber 16 in such a manner that the fluorescence entrance face 17a of the fluorescence transmission optical fiber 17 projects more toward the condenser lens group 30 than the laser light output face 16a of the laser light transmission optical fiber 16.

The condenser lens group 30 is configured in the same manner as in the first embodiment. Pulse laser light L transmitted through the laser light transmission optical fiber 16 and output from the laser light output face 16a is condensed by the condenser lens group 30 and is irradiated onto the surface of the analysis object 12.

The fluorescence F emitted from the atoms contained in the surface of the analysis object 12 enters the condenser lens group 30. The condenser lens group 30 condenses the fluorescence and guides it to the fluorescence entrance face 17a of the fluorescence transmission optical fiber 17.

As described above, the fluorescence F emitted from the atoms contained in the surface of the analysis object 12 can be condensed by the condenser lens group 30 and guided to the fluorescence entrance face 17a of the fluorescence transmission optical fiber 17. Accordingly, it is possible to achieve a sufficient performance although the light gathering rate of fluorescence F decreases a little and make the optical system unit 13 more compact.

Arranging the fluorescence entrance face 17a of the fluorescence transmission optical fiber 17 so as to project more toward the condenser lens group 30 than the laser light output face 16a of the laser light transmission optical fiber 16 makes it possible to prevent the pulse laser light L from entering the fluorescence entrance face 17a of the fluorescence transmission optical fiber 17 and improve the light gathering rate of the fluorescence F.

Figure 12:
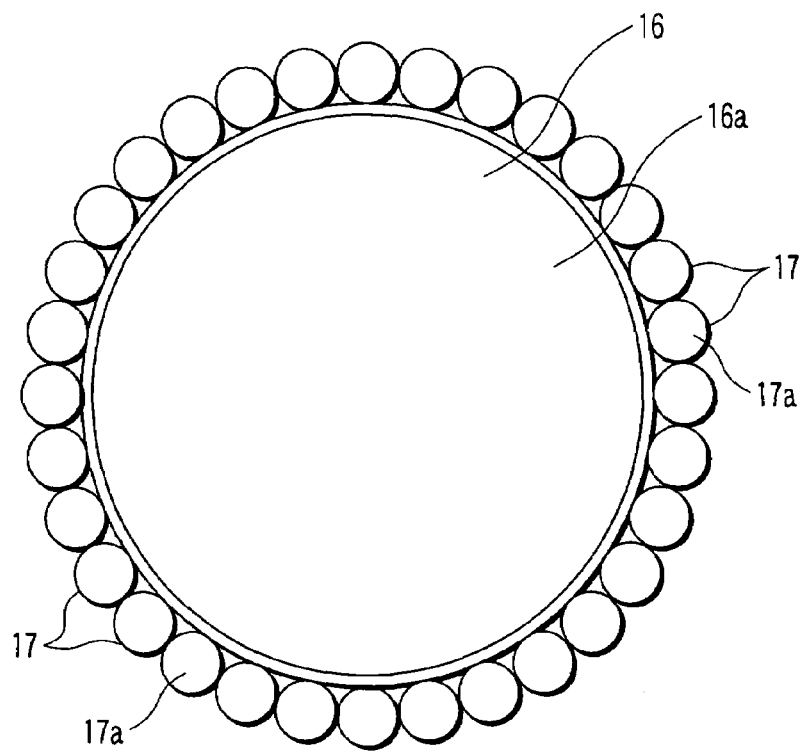
FIG. 12 is an end view showing the locational relationship between a laser light transmission optical fiber and a fluorescence transmission optical fiber in the analysis apparatus of the seventh embodiment.
Figure 11:
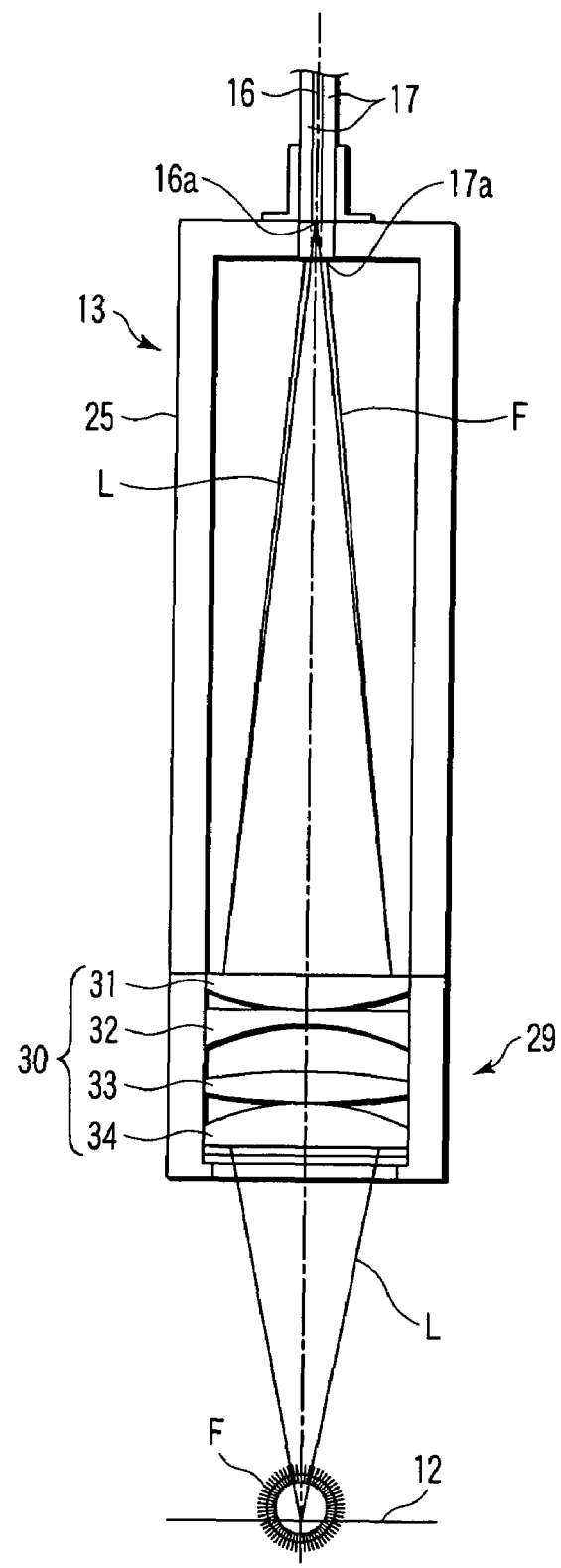
FIG. 11 is a sectional view of an optical system unit of an analysis apparatus according to a seventh embodiment of the present invention.

Next, FIGS. 11 and 12 show a seventh embodiment of the present invention. An optical system unit 13 has a body tube 25. At the rear anchor of the body tube 25, there are provided a laser light transmission optical fiber 16 and a plurality of fluorescence transmission optical fibers 17. At the tip of the body tube 25, there is provided a condenser lens group 30.

The laser light transmission optical fiber 16 is provided so as to correspond to the position of the axis line of the body tube 25. Each of the fluorescence transmission optical fibers 17 is formed so as to have a smaller diameter than that of the laser light transmission optical fiber 16. The fluorescence transmission optical fibers 17 are arranged around the laser light transmission optical fiber 16 in such a manner that the fluorescence entrance face 17a of each of the fluorescence transmission optical fibers 17 projects more toward the condenser lens group 30 than the laser light output face 16a of the laser light transmission optical fiber 16.

The condenser lens group 30 is configured in the same manner as in the first embodiment. A fluorescence measuring instrument 19 measures the wavelength and intensity of the fluorescence F transmitted through the plurality of fluorescence transmission optical fibers 17. Pulse laser light L transmitted through the laser light transmission optical fiber 16 and output from the laser light output face 16a is condensed by the condenser lens group 30 and is irradiated onto the surface of the analysis object 12.

The fluorescence F emitted from the atoms contained in the surface of the analysis object 12 enters the condenser lens group 30. The condenser lens group 30 condenses the fluorescence and guides it to the fluorescence entrance faces 17a of the plurality of fluorescence transmission optical fibers 17.

As described above, the fluorescence F emitted from the atoms contained in the surface of the analysis object 12 can be condensed by the condenser lens group 30 and guided to the fluorescence entrance faces 17a of the plurality of fluorescence transmission optical fibers 17. Accordingly, it is possible to achieve a sufficient performance although the light gathering rate of fluorescence F decreases a little and make the optical system unit 13 more compact.

Arranging the fluorescence entrance face 17a of each of the fluorescence transmission optical fibers 17 so as to project more toward the condenser lens group 30 than the laser light output face 16a of the laser light transmission optical fiber 16 makes it possible to prevent the pulse laser light L from entering the fluorescence entrance face 17a of each of the fluorescence transmission optical fibers 17 and improve the light gathering rate of the fluorescence F.

The present invention is not limited to the embodiments described above. When the present invention is reduced to practice, the structural elements can be modified without departing from the spirit and scope of the invention.

In addition, various inventions can be made by properly combining the structural elements of the embodiments.

Some of the structural elements of each embodiment may be omitted, and structural elements of different embodiments may be properly combined.

What is claimed is:

1. An analysis apparatus comprising:
a laser light transmission optical fiber which transmits laser light;
an optical system unit which includes:
(a) shaping means for shaping the laser light into a predetermined shape,
(b) distribution means for allowing the laser light having the predetermined shape transmitted through the laser light transmission optical fiber to pass through and reflect fluorescence emitted as a result of the irradiation of the laser light onto an analysis object, and
(c) condensing means for: (i) condensing the laser light shaped into the predetermined shape and passing through the distribution means and irradiating the condensed laser light onto the analysis object, and (ii) condensing the fluorescence from the analysis object and guiding the condensed fluorescence to the distribution means, in which the distribution means is provided between the condensing means and the shaping means;
a fluorescence transmission optical fiber which transmits the fluorescence reflected by the distribution means; and
analysis means for determining quantity of elements included in the analysis object on the basis of the fluorescence transmitted through the fluorescence transmission optical fiber;
wherein the shaping means shapes the laser light into an annulus.

2. The analysis apparatus according to claim 1, wherein the shaping means is a conical lens.

3. The analysis apparatus according to claim 2, wherein the shaping means is provided in an output end of the laser light transmission optical fiber.

4. An analysis apparatus comprising:
a laser light transmission optical fiber which transmits laser light;
an optical system unit which includes:
(a) shaping means for shaping the laser light into a predetermined shape,
(b) distribution means for allowing the laser light having the predetermined shape transmitted through the laser light transmission optical fiber to pass through and reflect fluorescence emitted as a result of the irradiation of the laser light onto an analysis object, and
(c) condensing means for: (i) condensing the laser light shaped into the predetermined shape and passing through the distribution means and irradiating the condensed laser light onto the analysis object, and (ii) condensing the fluorescence from the analysis object and guiding the condensed fluorescence to the distribution means, in which the distribution means is provided between the condensing means and the shaping means;
a fluorescence transmission optical fiber which transmits the fluorescence reflected by the distribution means; and
analysis means for determining quantity of elements included in the analysis object on the basis of the fluorescence transmitted through the fluorescence transmission optical fiber;
wherein the shaping means is a toroidal lens group for the shaping pulse laser light into a line.

5. An analysis apparatus comprising:
a laser light transmission optical fiber which transmits laser light;
an optical system unit which includes:
(a) shaping means for shaping the laser light into a predetermined shape,
(b) distribution means for allowing the laser light transmitted through the laser light transmission optical fiber and shaped into the predetermined shape by the shaping means to pass through and reflecting fluorescence emitted as a result of the irradiation of the laser light onto an analysis object,
condensing means for: (i) condensing the laser light shaped into the predetermined shape and passing through the distribution means and irradiating the condensed laser light onto the analysis object and (ii) condensing the fluorescence from the analysis object and guiding the condensed fluorescence to the distribution means in which the distribution means is provided between the condensing means and the shaping means, and reflecting means for reflecting the fluorescence reflected at the distribution means in a direction different from the direction in which the fluorescence was reflected;

a fluorescence transmission optical fiber which transmits the fluorescence reflected by the reflecting means; and analysis means for determining quantity of elements included in the analysis object on the basis of the fluorescence transmitted through the fluorescence transmission optical fiber;

wherein the shaping means shapes the laser light into an annulus.

6. The analysis apparatus according to claim 5, wherein the shaping means is a conical lens.

7. The analysis apparatus according to claim 6, wherein the shaping means is provided in an output end of the laser light transmission optical fiber.

8. An analysis apparatus comprising:

a laser light transmission optical fiber which transmits laser light;

an optical system unit which includes:
  (a) shaping means for shaping the laser light into a predetermined shape,
  (b) distribution means for allowing the laser light transmitted through the laser light transmission optical fiber and shaped into the predetermined shape by the shaping means to pass through and reflecting fluorescence emitted as a result of the irradiation of the laser light onto an analysis object, condensing means for: (i) condensing the laser light shaped into the predetermined shape and passing through the distribution means and irradiating the condensed laser light onto the analysis object and (ii) condensing the fluorescence from the analysis object and guiding the condensed fluorescence to the distribution means in which the distribution means is provided between the condensing means and the shaping means, and reflecting means for reflecting the fluorescence reflected at the distribution means in a direction different from the direction in which the fluorescence was reflected;

a fluorescence transmission optical fiber which transmits the fluorescence reflected by the reflecting means; and analysis means for determining Quantity of elements included in the analysis object on the basis of the fluorescence transmitted through the fluorescence transmission optical fiber;

wherein the shaping means is a toroidal lens group for the shaping pulse laser light into a line.

* * * * *